(12) United States Patent
Makino et al.

(10) Patent No.: US 6,368,807 B2
(45) Date of Patent: Apr. 9, 2002

(54) THREADING INTERCALATOR HAVING OXIDATION-REDUCTION ACTIVITY

(75) Inventors: Yoshihiko Makino, Saitama; Kazunobu Takahashi, Kanagawa; Makoto Takagi, Fukuoka; Shigeori Takenaka, Fukuoka; Kenichi Yamashita, Fukuoka, all of (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/733,365

(22) Filed: Dec. 8, 2000

(30) Foreign Application Priority Data

Dec. 8, 1999 (JP) ............................................. 11-349284

(51) Int. Cl.$^7$ .......................... C12Q 1/68; C07H 21/02; C07H 21/04; G01N 15/06
(52) U.S. Cl. ............................. 435/6; 422/50; 422/68.1; 536/25.3; 536/25.32; 536/26.6
(58) Field of Search ................................. 435/6; 422/50, 422/68.1; 536/25.3, 25.32, 26.6

Primary Examiner—Jezia Riley
(74) Attorney, Agent, or Firm—Reed Smith LLP

(57) ABSTRACT

A compound of the following formula:

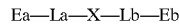

$$Ea-La-X-Lb-Eb$$

in which each of Ea and Eb independently is a group having oxidation-reduction activity and having a conjugated system in its group; X is a divalent cyclic group; and each of La and Lb independently is a group which does not form a conjugated system in combination with the conjugated system of each of Ea and Eb and at least one of which has a site imparting water solubility to the compound or a site that is convertible into a site imparting water solubility to the compound, is favorably employable as an electroconductive threading intercalator in an electrochemical method for detecting complementary DNA fragments.

12 Claims, No Drawings

THREADING INTERCALATOR HAVING OXIDATION-REDUCTION ACTIVITY

FIELD OF THE INVENTION

The present invention relates to a compound which is favorably employable as an electrochemically active threading intercalator in a procedure of analyzing oligonucleotides or polynucleotides such as DNA fragments.

BACKGROUND OF THE INVENTION

In the gene analysis in the fields of biochemistry and clinical test, the detection of a DNA or its fragment having a specific base sequence is performed by way of a hybridization method, particularly Southern hybridization method (Southern blotting method). Southern hybridization is performed using a radioisotope (RI) label. The conventional analytical methods using radioisotope label such as Southern hybridization method are disadvantageous in that they need troublesome radioisotopes.

A Southern hybridization method using a fluorescent label in place of a radioisotope label is also known. This method is superior to the method using RI in safety and rapidness. Therefore, DNA chips comprising a substrate such as a slide glass or a silicone plate and a great number of oligonucleotide or polynucleotide molecules fixed onto the substrate are now commercially available for the use in the fluorescence detection systems. However, the fluorescence detection system has other disadvantageous features, that is, the fluorescent label is. gradually faded out under irradiation of stimulating rays; a specifically designed fluorescence-measuring apparatus should be installed; and an amount of a fluorescent label is restricted because internal quenching takes place Recently, a new system for detection of DNA fragments which utilizes an electrode sensor onto which a group of probes comprising oligonucleotide molecules or polynucleotide molecules are fixed has been proposed in Japanese Patent Provisional Publication No. H9-288080 and Preprint of 57th Conference of Analytical Chemistry, pp. 137–138 (1996). In this system, an electrode which has an output terminal and further has he probe molecules fixed onto its surface is brought into contact with a DNA sample in an aqueous medium in the presence of a threading intercalator, and an electric current produced by applying an electric voltage between the electrode and another electrode introduced in the aqueous medium is measured.

As the threading intercalator, an electroconductive ferrocene-containing compound having oxidation-reduction activity (redox activity) which has the following chemical structure and can be specifically bonded to a hybrid or hybridized DNA is known:

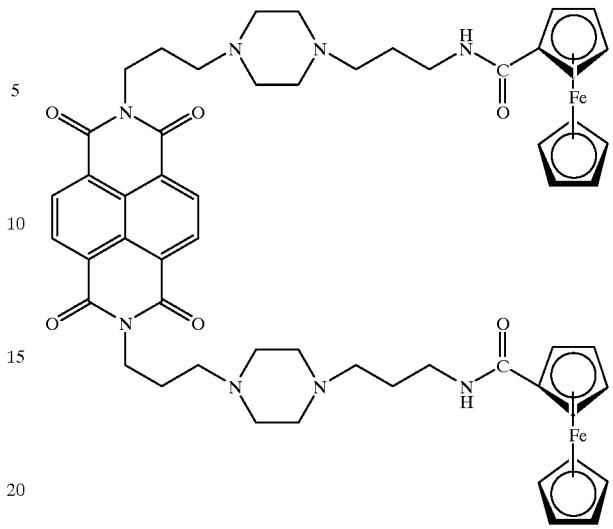

The above-mentioned electrochemical detection system utilizing an electrode sensor is advantageous in easily detecting the hybrid DM structure on real-time basis. No fading-out takes place.

The above-illustrated conventional electroconductive threading intercalator has a structure comprising a core portion of a naphthalene-diimide cyclic group, a pair of linker porions each of which is attached to each of the two ends of the core portion, and a pair of electroconductive ferrocene moieties each of which is attached to other end of each linker. The ferrocene moiety has an oxidation-reduction activity and a conjugated system in which electrons freely move.

In the procedures for detecting DNA fragments complementary to the probe molecules fixed on the electrode, the amount of electric current produced by the application of electric potential to the electrode essentially depends on the nature of an electroconductive threading intercalator, though in part depends on the natures of probe molecules and DNA fragment samples, and the ionic concentration of the buffer solution employed in the detection procedure. In the use of the conventional threading intercalator of the above-mentioned formula, a peak electric current is observed when an electric potential in the range of approx. 450 to 620 mV is applied. Therefore, in the detection procedures utilizing the conventional threading intercalator, an electric potential of approx. 450 mV or higher should he applied.

The electric potential of approx. 450 mV or higher is relative high for current detection devices. Accordingly, the cost for producing the detection devices for the electrochemical analysis of DNA fragments is relatively high. Moreover, if the probe molecules are attached to the electrode surface by weak bonding such as electrostatic bonding, the probe molecules are apt to be released from the electrode when a high electric potential is applied to the electrode. The release of the probe molecules from the electrode adversely effect to the detection sensitivity and detection accuracy. Particularly, the easy release of the probe molecules from the electrode adversely effect when the DNA chip is repeatedly employed in the detection procedures after the temporarily fixed DNA fragment samples and threading intercalator are removed.

Accordingly, it is an object of the invention to provide an electroconductive threading intercalator which is favorably employable in the electrochemical method for detecting polynucleotide samples or oligonucleotide samples (such as DNA fragments) by means of a DNA chip comprising an electrode and probe molecules (such as nucleo-tide derivatives or their analogues)

Specifically, it is an object of the invention to provide an electroconductive threading intercalator which is capable of working in the electrochemical detection procedure at a low electric potential applied to the electrode

SUMMARY OF THE INVENTION

The present invention resides in a compound having the formula (1):

$$Ea—La—X—Lb—Eb \quad (1)$$

in which each of Ea and Eb independently is a group having oxidation-reduction activity and having a conjugated system in its group; X is a divalent cyclic group; and each of La and Lb independently is a group which does not form a conjugated system in combination with the conjugated system of each of Ea and Eb and at least one of which has a site imparting water solubility to the compound or a site that is convertible into a site imparting water solubility to the compound.

In the above-mentioned formula, it is preferred that Ea is the same as Eb, and La is the same as Lb. The main chain of La—X—Lb preferably contains 10 to 100 atom, more preferably 15 to 70, most preferably 20 to 50, which are counted along the shortest connection route from Ea to Eb. For the sake of reference, the main chain of the aforementioned conventional threading intercalator has 32 carbon atoms.

The compound of the formula (1) preferably has the following formula (2):

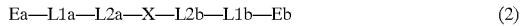

$$Ea—L1a—L2a—X—L2b—L1b—Eb \quad (2)$$

in which each of Ea and Eb independently is a group having oxidation-reduction activity and having a conjugated system in its group; x is a divalent cyclic group; each of L1a and L1b independently is a group which does not form a conjugated system in combination with the conjugated system of each of Ea and Eb; and each of L2a and L2b independently contains a linking group having a site imparting water solubility to the compound or a site that is convertible into a site imparting water solubility to the compound.

It is preferred that each of Ea and Eb of the formulas (1) and (2) independently a group having oxidation-reduction activity which is selected from the group consisting of a metallocene moiety, a 2,2'-bipyridine complex moiety, a cyclobutadiene moiety, a cyclopentadiene moiety, a 1,10-phenanthroline moiety, a triphenylphosphine moiety, a cathecol amine moiety, and a biologen moiety. Any of these moieties may have one or more substituents.

In the formula (2), it is preferred that each of L1a and L1b independently is a hydrocarbyl group which may have one or more substituents. The hydrocarbyl group preferably has 1 to 6 carbon atoms in its main chain, More specifically, it is preferred that each of L1a and L1b independently is an alkylene group having 1 to 6 carbon atoms or an alkenylene group having 2 to 6 carbon atoms. Each group may have one or more substituents.

In the formula (2), it is preferred that each of L2a and L2b independently is a linking group containing an atomic element other than carbon element. It is particularly preferred that each of L2a and L2b independently is a linking group containing N, O, or S. Specifically, it is preferred that each of L2a and L2b independently contains a linking group selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, and 1,4-piperazinyl bonding, any bonding possibly having one or more substituents. Most preferred is that each of L2a and L2b independently contains —NHICO— or —CONH—.

In the formula (2), it is preferred that Ea is the same as Eb, L1a is the same as L1b, and L2a is the same as L2b.

The invention also resides in an electroconductive threading intercalator having oxidation-reduction activity which is represented by the aforementioned formula (1) or (2).

The invention further resides in an electrochemical method for detection of oligonucleotide samples or polynucleotide samples which employs the above-mentioned threading intercalator of the invention.

The invention furthermore resides in a process for electrochemically detecting oligonucleotide samples or polynucleotide samples complementary to a group of probe molecules of nucleotide derivatives or their analogues fixed onto an electrode substrate, which comprises the steps of:

bringing the group of probe molecules into contact with oligonucleotide samples or polynucleotide samples in an aqueous medium in the presence of a threading intercalator so as to form by hybridization a complex of the group of probe molecules and the oligonucleotide samples or polynucleotide samples in which the threading intercalator is intercalated;

and detecting an electric current produced by applying an electric potential to the electrode substrate.

The invention furthermore resides in a process for electrochemically detecting oligonucleotide samples or polynucleotide samples complementary to a group of probe molecules of nucleotide derivatives or their analogues fixed onto an electrode substrate, which comprises the steps of:

bringing the group of probe molecules into contact with oligonucleotide samples or polynucleotide samples in an aqueous medium so as to form by hybridization a complex of the group of probe molecules and the oligonucleotide samples or polynucleotide samples;

bringing a threading intercalator according to claim 15 in contact with the formed complex so as to intercalate the intercalator into the complex;

and detecting an electric current produced by applying an electric potential to the electrode substrate.

In the above-mentioned processes, it is advantageous that the electric potential applied to the electrode substrate is in the range of 100 to 400 mV.

The invention furthermore resides in a kit for electrochemically detecting oligonucleotide samples or polynucleotide samples complementary to a group of probe molecules of nucleotide derivatives or their analogues fixed onto an electrode substrate, which comprises an electrode substrate having a group of probe molecules of nucleotide derivatives or their analogues fixed to its substrate, and an electroconductive threading intercalator of the invention It is preferred that the nucleotide derivatives and their analogues are oligonucleotides, polynucleotides, or peptide nucleic acids.

DETAILED DESCRIPTION OF THE INVENTION

The present inventors have assumed that the high electric potential is required in the electrochemical detection of DNA fragment samples using the conventional electroconductive threading intercalator because the conjugated system present in the electroconductive moiety such as a ferrocene moiety extends to the π electron-bonding group of the amide group (i.e., —NHCO—), so that the electron density of electrons moving in the conjugated system of the ferrocene moiety decreases. Based on the assumption, the inventors have synthesized a new electroconductive threading intercalator in which the conjugated system of the electroconductive ferrocene moiety is present independently of the π electron-bonding group of the amide group, and studied the function of the newly synthesized intercalator in the electrochemical detection of DNA fragment samples. It has been confirmed that the newly synthesized electroconductive intercalator gives a peak electric current at an expected low electric potential in the electrochemical detection.

The present invention has been made upon the above-mentioned discovery.

As described hereinbefore, the compounds which function as electroconductive threading intercalators in the electrochemical detection of DNA fragment samples have the formula (1), particularly the formula (2):

Ea—La—X—Lb—Eb     (1)

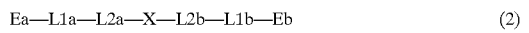

Ea—L1a—L2a—X—L2b—L1b—Eb     (2)

In the formulas (1) and (2), X represents a divalent cyclic group which may have one or more substituents.

The divalent cyclic group preferably is a plane cyclic group. Examples of the divalent cyclic groups include a naphthalene diimide group having two bonding sites at its two nitrogen atoms, an anthracene group having two bonding sites at 2- and 6-positions or 1- and 5- positions (preferably 2- and 6-positions), an anthraquinone group having two bonding sites in the same manner as in the anthracene group, a fluorene group having two bonding sites at 2- and 6-positions, a biphenylene group having two bonding sites at 2- and 6-positions, a phenantholene group having two bonding sites at 2- and 7-positions, and a pyrene group having two bonding sites at 2- and 7-positions. Preferred is a naphthalene diimide group having two bondings at the nitrogen atoms. The substituent can be a halogen atom (e.g., F, Cl, or Br), or an alkyl group having 1 to 6 carbon atoms such as methyl, ethyl, or n-propyl.

In the formula (1), each of La and Lb independently is a group which does not form a conjugated system in combination with the conjugated system of each of Ea and Eb and at least one of which has a site imparting water solubility to the compound or a site that is convertible into a site imparting water solubility to the compound. The site that is convertible into a site imparting water solubility to the compound means such site that it can be converted into a site imparting water solubility to the compound, for instance, by contact with an aqueous acidic solution such as an aqueous sulfuric acid. For instance, an imino group having a methyl substituent can be converted into a site having a sulfate group by contact with sulfuric acid. Thus formed site having a sulfate group imparts to the compound a necessary water solubility. The site can have an electric charge.

The water solubility is required for the compound in the case that the compound functions in an aqueous medium as the threading intercalator.

Each of La and Lb preferably has a hydrocarbyl group (which may have one or more substituents) on the side adjacent to Ea and Eb, respectively. The hydrocarbyl group corresponds to L1a and L1b of the formula (2) and further has a group having atomic elements other than carbon atoms on the side adjacent to X. The latter group corresponds to L2a and L2b of the formula (2). Accordingly, La and Lb are preferably represented by —L1a—L2a— and —L1b—L2b—, respectively.

Each of L1a and L1b preferably is an alkylene group having 1 to 6 carbon atoms or an alkenylene group having 2 to 6 carbon atoms, provided that each group may have one or more substituents. Each of L2a and L2b preferably is a linking group containing N, O or S.

Examples of the substituents for L1a and L1b include hydroxyl, halogen, carboxyl, amino, cyano, nitro, formyl, formylamino, alkl having 1 to 6 carbon atoms, alkylamio having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbo atoms which has 1 to 4 hetero atoms such as S, N, or O, and aryl having 6 to 12 carbon atoms in its ring structure which may have 1 to 5 substituents such as alkyl of 1–6 carbon atoms, alkoxy of 1–6 carbon atoms, or halogen. The number of the substituents preferably is in the range of 1 to 12, more preferably 1 to 3, when the main chain is an alkylene group having 1 to 6 carbon atoms. The number of the substituents preferably is in the range of 1 to 10, preferably 1 to 3, when the main chain is an alkenylene group having 2 to 6 carbon atoms.

Each of L2a and L2b preferably is a linking group containing one or more groups such as an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents. Each of L2a and Ub preferably contains —NHCO— or —CONH—.

Examples of the substituents for L2a and L2b include alkyl having 1 to 3 carbon atoms (e.g., methyl or ethyl), acyl having 2 to 4 carbon atoms (e.g., acetyl), aryl having 6 to 20 carbon atoms (e.g., phenyl or naphthyl), and aralkyl having 7 to 23 carbon atoms which has alkyl of 1–3 carbon atoms (e.g, benzyl).

When L2a or L2b contains an imino bonding, the imino bonding preferably contains a methyl substituent. Accordingly, each of L2a and L2b preferably is N-methyl-di(n-propylenyl)imino or 1,4-di(n-propylenyl)piperazinyl. Most preferred is N-methyl-di(n-propylenyl)imino.

Each of Ea and Eb has oxidation-reduction activity so that each has electroconductivity It is preferred that each of Ea and Eb independently is a metallocene moiety, a 2,2'-bipyridine complex moiety, a cyclobutadiene moiety, a. cyclopentadiene moiety, a 1,10-phenanthroline moiety, a triphenylphosphine moiety, a cathecol amine moiety, and a biologen moiety. Any moieties may have one or more substituents. Preferred are ferrocene moieties which may have one or more substituents. Examples of the substituted ferrocene moieties are illustrated below.

(F1)

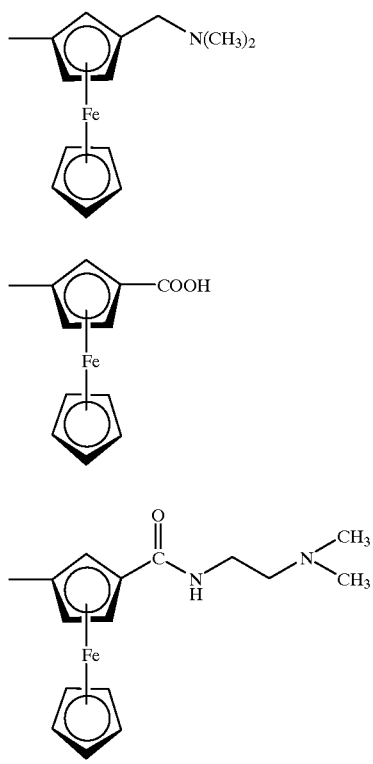

(F2)

(F3)

In the above-illustrated substituted ferrocene moieties, the substituent may be present in other positions on the cyclopentadienyl group.

The compound of the invention which is favorably employed as an electroconductive threading intercalator can be prepared by a process similar to the process described in the aforementioned Japanese Patent Provisional Publication No. H9-288080.

Alternatively, the compound of the invention can be efficiently synthesized from a known diamine compound in accordance with the following synthesis route:

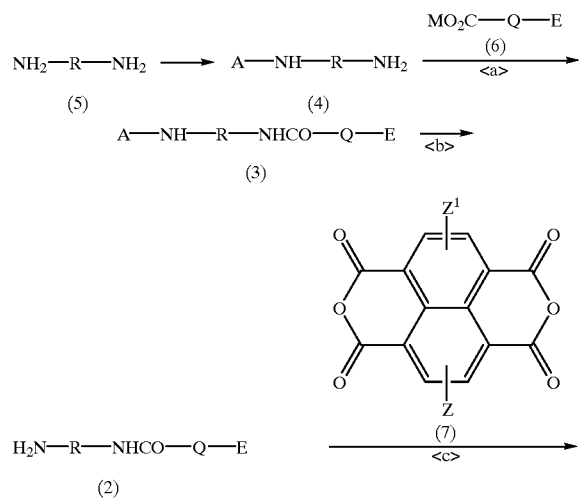

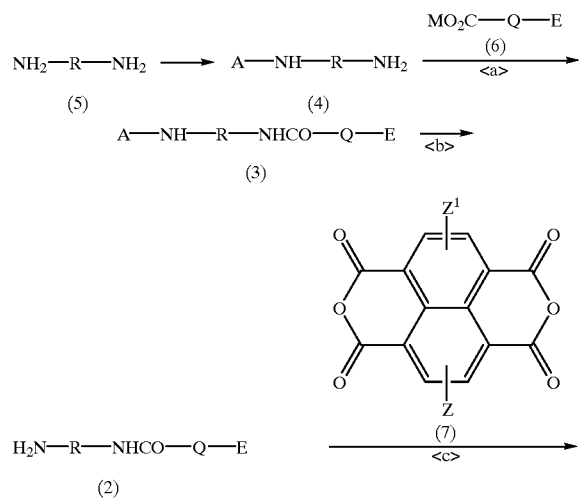

(1)

The above-illustrated synthesis route comprises three reactions <a>, <b>, and <c>. Although the core portion (i.e., naphthalene diimide structure) can have linkers differing from each other which is synthesized two different diamine compounds, the synthesis procedures are described for its representative compound having a symmetric structure.

The reactions participating in the synthesis route are explained below.

The compound (4), namely, A—NH—R—$NH_2$, can be synthesized from a known diamine (5) by the known method described in Green T. W., P.G.M., Protective Groups in Organic Synthesis (2nd Edition, Wiley, N.Y., 1991, 315–345, 349–359). "A" preferably is acyl having 2 to 5 carbon atoms, alkoxycarbonyl having 2 to 5 carbon atoms, benzoyl which may have one or more substituents, or benzyloxycarbonyl which also may have one or more substituents. Preferred are acetyl, t-butylcarbonyl (i.e., pivaloyl), t-butoxycarbonyl, or benzyloxycarbonyl possibly having one or more substituents. Examples of the substituents possibly attached to the benzoyl or benzyloxycarbonyl include halogen atoms, hydroxyl, alkyl having 1 to 6 carbon atoms, and alkoxy having 1 to 6 carbon atoms. The number of the substituents preferably is in the range of 1 to 5. Most preferred is 1.

The protected amine (4) can be generally obtained by the reaction of the diamine compound (5) with an acid halide or an acid anhydride having a moiety of A. Preferred examples of the acid halides and acid anhydrides are reactive reagents having a releasable group such as benzotriazol-1-yl-oxy (OBt), succinimidyloxy (OSu), or 3-thiazolidine-2-thion. Preferred reagent is 3-benzyloxycarbonyl-1,3-thiazoline-2-thion. The diamoin (5) is employed in an excessive amount as compared with the above-mentioned reactive reagent, such as 3 to 10 molar times.

The reaction can be performed in the presence of an organic base or an inorganic base. Examples of the organic bases include pyridine, triethylamine, and diisopropylethylamine. Examples of the inorganic bases include sodium hydroxide, potassium hydroxide, sodium hydrogen carbonate, sodium carbonate, and potassium carbonate. The base is preferably employed in a molar amount of 0.1 to excessive amount, more preferably 1 to 10 molar amounts, per one molar amount of the reactive reagent such as an acid halide.

The reaction is preferably carried out in a solvent, but the reaction can be carrier out in the absence of a solvent. The solvent should dissolve all or a portion of the reactive compounds and the reaction products and does not participate in the reaction. Examples of the solvents include alcohols (e.g., methanol, ethanol, isopropyl alcohol, and ethylene glycol), amides (e.g., dimethylformamide, dimethylacetamide, acetamide, and N-methylpyrrolidone), nitrites (e.g., acetonitrile and n-butylonitrile), ethers (e.g., ethylene glycol monomethyl ether, ethylene glycol monoethyl ether, tetrahydrofuran, eand dioxane), dimethylsulfoxide, sulforane, and water. The solvents can be employed in combination.

The reaction can be performed under chilling conditions or heated conditions. Generally, the reaction is performed at a temperature in the range of $-50°$ C. to $150°$ C., preferably $-10°$ C. to $100°$ C.

The compound (3), that is, A—NH—R—NHCO—Q—E, can be prepared by condensing the protective amine compound (4) with $MO_2C$—Q—E or $M^1OC$—Q—E - - - Reaction <a>. M is hydrogen, alkali metal (e.g., Na, K), and an imide having a bonding site at the nitrogen atom, such as succinimide, phthalimide, or glutalimide. $M^1$ is an active group such as halogen, —$SO_2Cl$, or a group corresponding to the below-mentioned reaction intermediate with the condensation reagent.

The reaction <a> is a condensation reaction between an amino group and a carboxyl group. The condensation reaction can be carried out in the manner described in Larock R. C., Comprehensive Organic Transformatims (VCH, New York, 1989, 972–97). The condensation reaction is preferably carried out using a condensating agent. The condensating agent preferably is 1,3-dicyclohexylcarbodiimide or 1-ethyl-3-(3'-dimethylamincpropyl)carbodiimide. The reaction can be preferably performed in the presence of a solvent. The solvent should dissolve whole or a portion of the reactive compounds and the reaction products and should no participate in the reaction. Examples of the employable solvents include, in addition to the solvents described for the aforementioned reaction <a>, halogen atom-containing solvents (e.g., dichloromethane, chloroform, and 1,2-dichloroethane) and esters (e.g., acetate esters). The organic solvents can be employed in combination. Water and a mixture of water and the organic solvent also can be favorably employed. In the reaction, the carboxylic acid (6) is preferably employed in an excessive amount compared with the compound (4) in 1 to 2 molar amounts. To the compound (4) is preferably added the compound of $M^1OC$—Q—E in an excessive amount such as 1 to 3 molar amounts.

When 1,3-dicyclohexylcarbodiimide or 1-ethyl-3-(3'-dimethylaminopropyl)carbodiimide is employed as the condensating agent, an acidic or basic additive can be used in combination. Preferred acidic additives are N-hydroxysuccinimide, N-hydroxybenzotriazole, and 3,4-dihydroxy-4-oxo-1,2,3-benzotriazine. Preferred basic additives are tertiary amines (e.g., triethylamine), pyridine, and 4-dimethylaminopyridine. The additive can be employed in an excessive amount such as 0.1 mole or extremely excessive amount, preferably 1 to 3 molar amount, per one mole of the condensating agent. The reaction can be carried out under chilling conditions or heated conditions. Generally, the reaction is performed at a temperature in the range of $-50°$ C. to $150°$ C., preferably $-10°$ C. to $100°$ C., more preferably 0 to $500°$ C.

The reaction <b> is performed for removal of the protective group of the amino group. The reaction for removing the protective group can be performed under conditions which are selected depending upon the nature of the protective group A. Generally, the reaction conditions described in the aforementioned Protective Groups in Organic Synthesis are employed. Preferred is a method using iodotrimethylsilane. The reaction is preferably performed in a solvent, but can be conducted in the absence of a solvent. The solvent should dissolve whole or a portion of the reactive compounds and the reaction products, and should not participate in the reaction. Examples of the solvents include halogenated solvents (e.g., dichloromethane and dichloroethane), nitrites (e.g., acetonitrile and n-butylonitrile), ethers (e.g., tetrahydrofuran and dioxane), aromatic solvents (e.g. toluene and benzene), and their mixtures. In the reaction, an excessive amount of iodotrimethylsilane [excessive compared with the compound (3)], such as 1 to 10 molar amount, is preferably employed. The reaction can be carried out under chilling conditions or heated conditions. Generally, the reaction is performed at a temperature in the range of $-50°$ C. to $150°$ C., preferably $-10°$ C. to $100°$ C., more preferably 0 to $50°$ C.

The reaction <c> is a reaction for condensating under dehydration the compound (2) with the naphthalenediimide core (7) to form side chains, so as to give the compound (1). The naphthalenediimide can be favorably prepared from 1,4,5,8-naphthalene tetracarboxylic acid dianhydride. The reaction can be performed in a solvent which should dissolve whole or a portion of the reactive compounds and the reaction products and should not participate in the reaction. Most of the aforementioned solvents are employable. In the reaction, two or more equivalent moles of the compound is preferably employed for one mole of 1,4,5,8-naphthalene tetracarboxylic dianhydride. Some solvents can be employed in an amount of less than the two equivalent moles. The reaction can be carried out under chilling conditions or heated conditions. Preferably, the reaction is performed at a temperature in the range of $0°$ C. to the reflux temperature of the employed solvent.

The electrochemical processes for detecting nucleic acid samples according to the invention are further described below.

The process of the invention for electrochemically detecting oligonucleotide samples or polynucleotide samples complementary to a group of probe molecules of nucleotide derivatives or their analogues fixed onto an electrode substrate, of the invention comprises the steps of:

bringing the group of probe molecules into contact with oligonucleotide samples or polynucleotide samples in an aqueous medium in the presence of a threading intercalator of the invention so as to form by hybridization a complex of the group of probe molecules and the oligonucleotide samples or polynucleotide samples in which the threading intercalator is intercalated;

and detecting an electric current produced by applying an electric potential to the electrode substrate Alternatively, the process of the invention comprises the steps of:

bringing the group of probe molecules into contact with oligonucleotide samples or polynucleotide samples in an aqueous medium so as to form by hybridization a complex of the group of probe molecules and the oligonucleotide samples or polynucleotide samples;

bringing a threading intercalator of the invention in contact with the formed complex so as to intercalate the intercalator into the complex;

and detecting an electric current produced by applying an electric potential to the electrode substrate.

The electrode employed for fixing probe molecules such should receive the probe molecules for fixing them onto the surface of the electrode. Preferred materials of the electrode are gold, glassy carbon, and carbon. In the practical use of the detection system of the invention, a number of electrodes are preferably combined to form one analytical chip.

The probe molecule which is a single stranded DNA fragment can be obtained from DNA or its fragment which is obtained by extraction from a living body, cleavage by restriction enzy, separation by electrophoresis, and denaturation by heat-treatment or alkaline-treatment. The single stranded oligonucleotide can be chemically synthesized., In any case, it is preferred that the single stranded probe oligonucleotide such as DNA fragment for the probe molecules is previously analyzed for base sequencing according to the known methods.

The probe molecule is then fixed onto an electrode. The fixation method is already known. For instance, a thiol group is attached to 5'- or 3'-terminal (5'-terminal is preferred) of the probe molecule, such as, oligonucleotide or polynucleotide, and the attached thiol coordinates a gold atoms of the electrode. The method for incorporating a thiol group to the DNA is described in M. Maeda et al., Chem. Lett., 1805–1806 (1994) and A. Connolly, Nucleic Acids Res., 13, 4484 (1985).

In the fixation process, the probe molecule having thiol terminal is dropped onto the gold electrode, and then the desired probe molecule is fixed on the electrode after allowing it to stand for a few hours at a low temperature.

In the use of a glassy carbon electrode, the electrode is oxidized by potassium permanganate to produce carboxyl groups on the surface of the electrode. On the surface having carboxyl groups is dropped the probe molecule having thiol terminal, so that an amide bondilng is formed to fix the probe molecule onto the surface of the glassy carbon electrode. Details of this method are described in K. M. Millan et al., Analytical Chemistry, 65, 2317–2323 (1993)

The hybridization is carried out in the presence of the electroconductive threading intercalator of the invention, which is preferably used in a concentration of several nM to several mM The intercalator can accelerate the hybridization between the probe oligonucleotide and a sample DNA fragment and per se inserts into the complex structure of the hybridized DNA so that the hybridized DNA is stabilized. Thus produced complex of the intercalator and the hybrid DNA can be understood as a polymer having on its side a number of ferrocene moieties. Thus aligned ferrocene moieties serve to assist the electron transfer between the electrode on which the probe molecules are fixed and a counter electrode which is placed in an aqueous solution in which the detection procedures are performed.

The fixation of the DNA fragment sample to the probe molecule of the electrode can be detected by applying an electric potential to the electrode of DNA chip. In the detection, a counter electrode is employed.

There are no specific limitations with respect to the electric potential applied to the electrode. However, since the hybride structure having the electroconductive threading intercalator of the invention gives a peak electric current even when a low electric potential such as 400 mV or lower is applied. Accordingly, it is advantageous to employ a electric potential in the range of 100 to 400 mV, particularly 200 to 400 mV for applying to the electrode of the DNA chip when the electrochemical detection procedure is performed.

The threading intercalator of the invention can be also favorably employable for detecting DNA fragment samples which are partly complementary to the probe molecules. Such fragment samples are generally referred to as "mis-match fragment". The detection of the mis-match fragment can be performed by comparing the strength of the peak current obtained in the detection of the possibly mismatched DNA fragment with the strength of the corresponding peak current obtained in the detection of a fully complementary DNA fragment (i.e., full-match fragment).

The present invention is further described by the following examples.

[Preparation of Threading Intercalator of Invention]
Preparation of N,N'-bis(7-ferrocene-acetamido-4-methyl-4-azaheptyl)naphthalene imide

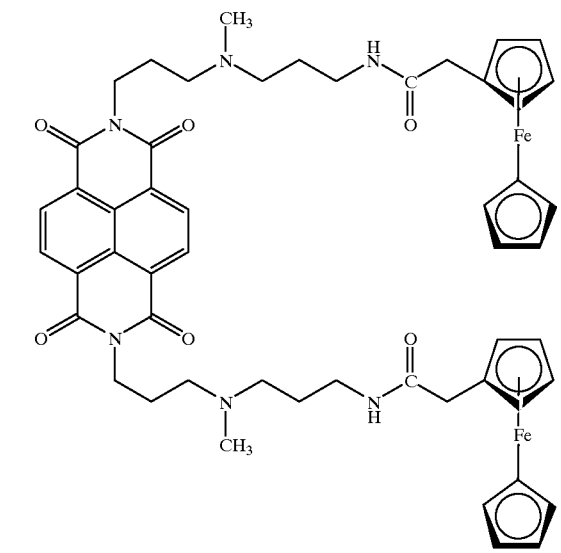

(1) Preparation of N-1-benzyloxycarbonyl-1,7-diamino-4-methyl-azaheptane

In dichloromethane (400 ml) was dissolved di(3-aminopropyl)-N-methylamine (73.0 g, 500 mmol.). To the resulting solution was dropwise added a solution of 3-benzyloxycarbonyl-1,3-thiazolidine-2-thione (12.8 g, 50 mmol., Synthesis, 1990, 27) in dichloromethane (100 mL). The mixture was stirred for 3 hours at room temperature. The resulting precipitate was removed by filtration. To the filtrate were added ethyl acetate and water. The aqueous mixture was then extracted twice with ethyl acetate. The ethyl acetate portion was combined and washed successively with water and saturated aqueous sodium chloride solution. The washed ethyl acetate portion was then subjected to extraction with two portions of 1 N aqueous hydrochloric acid. The obtained aqueous portions were combined and washed with ethyl acetate. To the aqueous portion was added 6 N aqueous sodium hydroxide solution under chilling to adjust the aqueous portion at pH 9–10. The alkaline solution was extracted with ethyl acetate. The ethyl acetate portion was washed with saturated aqueous sodium chloride solution, dried over anhydrous sodium sulfate, and placed under reduced pressure to distill the solvent out, so as to obtain 9.4 g of the desired product, yield 66%.

$^1$H-NMR (300 MHz, CDCl$_3$) δ: 1.58–1.72 (4H, m), 2.20 (3H, s), 2.35–2.45 (4H, m), 2.64 (2H, t), 3.23–3.32 (2H, m), 5.15 (2H, s), 7.22–7.45 (5H, m).

MS:FAB 280 (M$^+$+1) (matrix: m-nitrobenzene)

(2) Preparation of N-1-benzyloxycarbonyl-1-amino-7-ferrocene-acetamido-4-methyl-4-azaheptane The N-1-benzyloxycarbonyl-1,7-diamino-4-methylazaheptane (3.0 g, 11 mmol.) obtained in (1) above was dissolved in dichloromethane (30 mL). To the resulting solution were added ferrocene-acetic acid (2.7 g, 11 mmol.), pyridine (2 mL) and ethyl N,N'-dimethylaminopropylcarbodiimide (2.3 g, 12 mmol.). The mixture was then stirred for 3 hours at room temperature. To the reaction mixture was added an aqueous ammonium chloride solution. The mixture was extracted twice with ethyl acetate, and the ethyl acetate portions were combined. The ethyl acetate portion was washed with saturated aqueous sodium chloride solution and placed under reduced pressure to distill the solvent off. The residual brown oil was processed by column chromatography (column: alumina, eluent: chloroform/methanol=20/1). The obtained crystalline product was washed with a mixture of hexane and ethyl acetate to give 2.6 g of the desired product (yield: 91%) as an orange-colored crystalline product.

$^1$H-NMR (300 MHz, CDCl$_3$) δ: 1.50–1.72 (4H, m), 2.08 (3H, s), 2.20–2.33 (4H, m), 3.15–3.30 (4H, m), 3.34 (2H, s), 4.15 (5H, s), 4.16 (4H, s), 5.15 (2H, s), 5.54 (1H, bs), 6.44 (1H, bs), 7.32–7.48 (5H, m).

(3) Preparation of 1-amino-7-ferrocene-acetamido-4-methyl-4-azaheptane

In acetonitrile (30 mL) was dissolved the N-1-benzyloxycarbonyl-1-amino-7-ferrocene-acetamido-4-methyl-4-azaheptane (1.6 g, 3.0 mmol.) obtained in (2) above. The mixture was stirred at room temperature, and to this stirred mixture was dropwise added trimethylsilane iodide (1.25 mL, 8.8 mmol.). After 5 minutes, 1 N aqueous hydrochloric acid and ethyl acetate were added to the reaction mixture. The reaction mixture was then extracted three times with 1 N aqueous hydrochloric acid. The aqueous portion was washed with ethyl acetate, and then chilled with ice. To the chilled aqueous portion was added 2N aqueous potassium hydroxide solution to adjust the aqueous solution to pH 10. The alkaline aqueous solution was extracted twice with chloroform. The chloroform portion was washed with saturated aqueous sodium chloride solution, and placed under reduced pressure to distill the solvent off, to give 1.0 g of the desired product (yield 70%) as a brown crystalline product.

$^1$H-NMR (300 MHz, CDCl$_3$) δ: 1.48–1.62 (4H, m), 2.09 (3H, s), 2.25–2.35 (4H, m), 2.71 (2H, t), 3.22–3.33 (2H, m), 3.35 (2H, s), 4.1–4.21 (9H, m), 6.75 (1H, bs).

(4) Preparation of N,N'-bis(7-ferrocene-acetamido-4-methyl-4-azaheptyl)naphthalene diimide In tetrahydrofuran (50 mL) was dissolved the 1-amino-7-ferocene-acetamiao-4-methyl-4-azheptane (0.95 g, 2.5 mmol.) obtained in (3) above. The mixture was stirred at room temperature. To the stirred mixture was added 1,4,5,8-tetracarboxylic acid naphthalene dianhydride (0.3 g, 1.1 mmol.). The mixture was then refluxed for 7 hours. The reaction mixture was filtered and washed with chloroform. The organic portions were combined and placed under reduced pressure. The resulting residue was processed by column chromatography (column: alumina, eluent: chloroform/methanol=15/1). The obtained crystalline product was washed with ethyl acetate to give 0.32 g of the desired product (yield: 30%) as a brown crystalline product.

$^1$H-NMR (300 Mz, CDCl$_3$) δ: 1.56–1.70 (8H, m), 1.78–1.92 (4H, m), 2.12 (6H, s), 2.33–2.46 (8H, m), 3.30–3.42 (4H, m), 3.36 (4H, s), 4.13 (10H, s), 4.20 (8H, s), 6.85 (2H, bs), 8.80 (4H, s).

MS:FAB 975 (M+H) (matrix: m-nitrobenzene)

EXAMPLE 1
Detection of Hybrid DNA Fragment
(1) Manufacture of Electrochemical Analytical Element On a gold electrode (surface area: 2.25 mm$^2$) was spotted 2 μL of an aqueous solution containing 100 picomol./μL of T$_{20}$ (thymine 20-mers having an aminohexyl group at its 55'-terminal). The spotted solution was allowed to stand for one hour at room temperature, and the unfixed T$_{20}$ was washed out, and dried, to give an electrochemical analytical element. The preparation of T$_{20}$ and its fixation were carried out in the manner described in the aforementioned Japanese Patent Provisional Publication No. H9-268080.

(2) Preparation of Ferocene-labeled Oligonucieotide
Adenine 20-mers (dA$_{20}$) sample was prepared in the mannter as described in the above-mentioned Publication, and employed as a DNA fragment sample.

(3) Detection of Hybrid DNA Fragment
On the analytical element prepared in (1) above was spotted 2 μL of a Tris buffer (10 mM, pH 7.5) containing the dA$_{20}$ obtained in (2) above. The analytical element was then kept at 25° C. for 20 minutes for performing incubation. The incubated element was washed with an aqueous solution of 0.1 M sodium dihydrogen phosphate-disodium hydrogen phosphate (pH 7.0) to remove the unfixed dA$_{20}$.

Thus treated element was placed in 0.1 M potassium chloride-0.1 M acetic acid buffer (pH 5.6) containing 50 μM of the threading intercalator prepared in the aforementioned preparation example, and subjected to differential pulse voltammetry (DVP) in the applied voltage range of 100 to 700 mV, pulse oscillation 50 mV, pulse width 50 ms, and a scanning rate 100 mV/sec. A responsive electric current as a peak value at 260 mV was detected.

For obtaining control current, the same procedures except for employing the intercalator were repeated.

The responsive electric current obtained at 260 mV using the intercalator of the invention is as high as 36%, as compared with the control current.

Comparison Example 1
Detection of Hybrid DNA Fragment
The same procedures as in Example 1 were repeated except for employing the conventional intercalator described in the aforementioned Japanese Patent Provisional Publication H9-288080. The responsive current as a peak value was detected at 460 mV.

The responsive electric current obtained at 460 mV using the conventional intercalator is as high as 38%, as compared with the control current.

The results of example 1 and comparison example 1 indicate that the threading intercalator of the invention gives at 260 mV a peak current strength which is almost equal to the peak current strength at 460 mV obtained in the use of the conventional threading intercalator.

EXAMPLE 2
Detection of Hybrid DNA Having Mis-match Structure
(1) Manufacture of Electrochemical Analytical Element
The procedures of example 1-(1) were repeated except for using dT$_{19}$G$_1$ (corresponding to mis-match oligonucleotide) to manufacture an analytical element.
(2) Detection of Hybrid DNA Having Mis-Match Structure
The procedures of Example 1-(3) and the procedures of Comparison Example 1 were repeated except for using the analytical element manufactured in (1) above, to give a peak electric current of 36% increased from the control value at 260 mV in the use of the intercalator of the invention, and a peak electric current of 20% increased from the control value at 260 mV in the use of the conventional intercalator.

What is claimed is:
1. A compound having the formula (1):

Ea—L1a—L2a—X—L2b—L1b—Eb    (1)

in which each of Ea and Eb independently is a group having oxidation-reduction activity and having a conjugated system in its group; X is a divalent cyclic group; each of L1a and L1b independently is a group which does not form a conjugated system in combination with the conjugated system of each of Ea and Eb; and each of L2a and L2b independently. is a linking group containing one or more groups selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents selected from the group consisting of alkyl having 1 to 3 carbon atoms, acyl having 2 to 4 carbon atoms, aryl having 6 to 20 carbon atoms, and aralkyl having 7 to 23 carbon atoms which has alkyl of 1–3 carbon atoms.

2. The compound of claim 1, wherein each of Ea and Eb independently a group having oxidation-reduction activity which is selected from the group consisting of a metallocene moiety, a 2,2'-bipyridine complex moiety, a cyclobutadiene moiety, a cyclopentadiene moiety, a 1,10-phenanthroline moiety, a triphenylphosphine moiety, a cathecol amine moiety, a biologen moiety, and a substituted ferrocene moiety having a structure selected from the group consisting of formulas I, II and III:

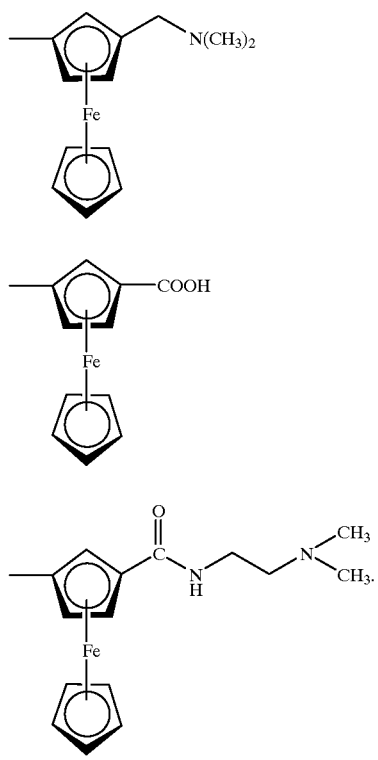

3. The compound of claim 1, wherein each of L1a and L1b independently is an alkylene group having 1 to 6 carbon atoms or an alkenylene group having 2 to 6 carbon atoms, each group possibly having one or more substituents, selected from the group consisting of hydroxyl, halogen, carboxyl, amino, cyano, nitro, formyl, formylamino, alkyl having 1 to 6 carbon atoms, alkylamino having 1 to 6 carbon atoms, halogenated alkyl having 1 to 6 carbon atoms, cycloalkylamino having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms, and aryl having 6 to 12 carbon atoms in its ring structure which may have 1 to 5 substituents selected from the group consisting of alkyl of 1–6 carbon atoms, alkoxy of 1–6 carbon atoms, or halogen.

4. The compound of claim 1, wherein each of L2a and L2b independently is a linking group containing N, O, or S.

5. The compound of claim 1, wherein each of L2a and L2b independently contains —NHCO— or —CONH—.

6. The compound of claim 1, wherein Ea is the same as Eb, L1a is the same as L1b, and L2a is the same as L2b.

7. A process for electrochemically detecting oligonucleotide samples or polynucleotide samples complementary to a group of probe molecules of nucleotide derivatives fixed onto an electrode substrate, which comprises the steps of:

bringing the group of probe molecules into contact with oligonucleotide samples of polynucleotide samples in an aqueous medium in the presence of the compound of claim 1 as a threading intercalator so as to form by hybridization a complex of the group of probe molecules and the oligonucleotide samples or polynucleotide samples in which the threading intercalator is intercalated; and detecting an electric current produced by applying an electric potential to the electrode substrate.

8. The process of claim 7, in which the electric potential applied to the electrode substrate is in the range of 100 to 400 mV.

9. A process for electrochemically detecting oligonucleotide samples or polynucleotide samples complementary to a group of probe molecules of nucleotide derivatives fixed onto an electrode substrate, which comprises the steps of:

bringing the group of probe molecules into contact with oligonucleotide samples or polynucleotide samples in an aqueous medium so as to form by hybridization a complex of the group of probe molecules and the oligonucleotide samples or polynucleotide samples;

bringing the compound of claim 1 as a threading intercalator in contact with the formed complex so as to intercalate the intercalator into the complex; and detecting an electric current produced by applying an electric potential to the electrode substrate.

10. The process of claim 8, in which the electric potential applied to the electrode substrate is in the range of 100 to 400 mV.

11. A kit for electrochemically detecting oligonucleotide samples or polynucleotide samples complementary to a group of probe molecules of nucleotide derivatives fixed onto an electrode substrate, which comprises an electrode substrate having a group of probe molecules of nucleotide derivatives fixed to its substrate, and the compound of claim 1 as a threading intercalator.

12. The kit of claim 11, in which the nucleotide derivatives are oligonulceotides, polynucleotides, or peptide nucleic acids.

* * * * *